(12) United States Patent
Casey (10) Patent No.: US 6,961,619 B2
(45) Date of Patent: Nov. 1, 2005

(54) SUBCUTANEOUSLY IMPLANTABLE POWER SUPPLY

(76) Inventor: Don E. Casey, 406 Thurber Dr. West, #9, Columbus, OH (US) 43215

( * ) Notice: Subject to any disclaimer, the term of this patent is extended or adjusted under 35 U.S.C. 154(b) by 558 days.

(21) Appl. No.: 10/190,950

(22) Filed: Jul. 8, 2002

(65) Prior Publication Data

US 2003/0004546 A1 Jan. 2, 2003

Related U.S. Application Data

(63) Continuation-in-part of application No. 09/650,503, filed on Aug. 29, 2000, now abandoned.

(51) Int. Cl.⁷ .............................................. A61N 1/378
(52) U.S. Cl. .............................. 607/61; 607/33; 607/36
(58) Field of Search ................................. 607/1, 2, 4–5, 607/9, 33–34, 36, 39–58, 61; 128/899

(56) References Cited

U.S. PATENT DOCUMENTS 3,672,352 A * 6/1972 Summers ..................... 600/476
5,199,429 A * 4/1993 Kroll et al. ..................... 607/5
5,800,478 A * 9/1998 Chen et al. ................... 607/88

* cited by examiner

Primary Examiner—Carl Layno
(74) Attorney, Agent, or Firm—David A. Greenlee (57) ABSTRACT

A subcutaneously implantable power supply is a device for powering implantable medical devices. The device has one or more thin photovoltaic cells contained in a case formed of a lamination of a plurality of thin plastic layers. Each layer is translucent in the area covering said cell, such that the power supply is sufficiently flexible to conform to body contours. The device is lightweight, flexible, has improved sealability, and has improved internal battery longevity.

14 Claims, 9 Drawing Sheets

SUBCUTANEOUSLY IMPLANTABLE POWER SUPPLY

RELATED APPLICATIONS

This application is a continuation-in-part of application Ser. No. 09/650,503, now abandoned, filed Aug. 29, 2000 now abandoned by the inventor herein, and identically titled.

BACKGROUND OF THE INVENTION

1. Field of the Invention

This invention relates to subcutaneous power supplies having photovoltaic cells, or solar cells, and, more particularly to such power supplies that prevent the ingress of bodily fluids, and have high spectral response after insertion under living tissue.

2. Background Art

There are several commercially-available electronic devices implanted in humans and animals that require a power source, typically Lithium-Ion (L-I, one rechargeable type) or Silver Vanadium Oxide (SVO) batteries.

These devices include: cardiac pacemakers; heart defibrillators; pain suppressors; drug infusion pumps (typically for insulin), augmentation mechanical heart pumps, retinal eye implant devices, limb implant devices, bodily valve switches, which is a partial list. Also, implantable hearing aid devices, with other transmitter-receiver devices in the planning stage.

One interesting new bodily implanted transmitter-receiver(s) bridges the gap over severed or damaged nerves in living organisms. Researchers at Reading University, England have implanted a glass tube beneath the skin of a subject. The tube contains a device that transmits signals outside the body; it is a forerunner to nerve-gap transmission of nerve impulse signals. These devices presently employ a battery within the implanted device, charged by an internal-external induction coil. Although external-internal induction coils will work as a method of recharging implanted batteries, they are far from ideal as a charging method, because of the impracticality of positioning an external coil, and the inconvenience of the wearer remaining physically close to the external coil for very long periods of time, necessary to trickle-charge the batteries.

The trickle-charging method requires a rapid recharging process, which always shortens battery life. Very slow trickle charging of batteries at a rate not to exceed the discharge rate of the implant device they power is ideal for maximum battery longevity.

The average age of cardiac pacemaker batteries is seven years, and the average age of the recipient is seventy-two. The entire device may require replacement at age seventy-eight, since the battery is sealed inside. These batteries are permanently sealed inside laser welded titanium pacemaker cases, thus requiring the entire unit be replaced at great cost. However, at age seventy-eight, the wearer's health has frequently deteriorated to the point where they cannot withstand the trauma of replacement surgery, which results in death in 10%–15% of the cases. Teenagers requiring pacemakers or defibrillators could tolerate replacement surgery up to fifteen times during their lives.

The batteries powering heart defibrillators generally deplete more rapidly than pacemakers because they must maintain a constant charge in the unit's capacitors. When a firing sequence begins, the defibrillator must impart a strong electrical charge to shock the heart repeatedly, until a stabilized pattern of beats has been reestablished. This firing sequence must be repeated in rapid succession frequently, requiring a fast re-charging cycle of the unit's (usually one or two) capacitors. The sudden current demand on a defibrillator tends to be greater than that of pacemakers. Defibrillator batteries frequently last only three to six years due to the voltage requirement of the capacitors—around 400 volts.

Other implanted electrically-driven devices, such as the insulin infusion pumps, have a shunt leading into the pancreas, and another exiting the side of the abdomen, where it plugs into an external plastic bag of insulin. The bag is worn on a separate belt positioned above a patient's clothing belt, so that the shunt tube will not be pinched off. This internal pump includes a sensing device which measures the blood sugar level and switches the pump on and off, injecting one or two drops of insulin into the pancreas per-actuation. Trickle-feeding insulin prevents large fluctuations in the insulin level of the blood, which is presently the case when syringes are used.

Mechanical hearts require more electrical power, because their drive motors must open and close valves or spin centrifugal impellers, providing the propulsive force to push blood through the body against the body's natural resistance due to blood being progressively forced through narrowing capillaries. The difficulty of this task is increased when the wearer is standing or moving. While standing, blood must be pumped up to the brain, a level higher than the mechanical heart, and must be pumped to the feet and its return path up the veins to the lungs, where it is re-oxygenated.

The power supplied for such devices requires, ideally, one rechargeable battery inside or near the mechanical heart, and a much larger battery pack worn externally. These outside batteries typically comprise a series of thin units wired in a string and sewn into a belt-like construction with wires exiting the body and attaching to them, or by having a small flat inverter-induction coil attached to the inside wall of the battery pack-belt. This outside induction coil must be axially positioned over a second induction coil-inverter implanted underneath the skin—opposite the belt. This permits current to jump across the two coils, after it is first converted from d.c. to a.c. power, then penetrating the dermis, and entering the body as a.c. current, where it is reconverted back to d.c. for transmittal by wires to the mechanical heart.

Cardiac pacemakers presently account for the most widespread use of internal batteries, typically single cell L-I types, although newer batteries are being introduced. The L-I battery generates a nominal 2.8 volts from a single cell when fresh, and is allowed to drop as little as 0.2 volts before replacement is indicated. However, depending on the construction of the cathode and anode plates, the L-I battery can generate up to 3.7 volts from a single cell.

More efficient electrical circuit designs have been made through the years, however, the added telemetry functions for implantable devices have tended to offset these efficiency gains. With external telemetry, the surgeon can change the rate (time-duration-width) and the intensity (voltage) of the beats in a non-invasive manner. Regardless of the improvements in electronically implantable batteries and devices, the wearer will want as few replacement surgeries as possible.

What has been needed but heretofore unavailable, is an improved subcutaneous device for powering implantable medical devices of all kinds that is lightweight, flexible, has improved sealability, and has improved internal battery longevity.

SUMMARY OF THE INVENTION

It is an object of this invention to provide an improved subcutaneous device for powering implantable medical devices of all kinds that is lightweight, flexible, has improved sealability, and has improved internal battery longevity.

In one aspect this invention features a device that improves the longevity of internal batteries contained within, and used in connection with, implantable medical devices. An implanted device adapted to be implanted subcutaneously within living tissue comprises a thin photovoltaic cell encased in a case formed of a lamination of a plurality of thin plastic layers, each layer being translucent in the area covering said cell, such that the power supply is sufficiently flexible to conform to body contours.

In another aspect this invention features a device that is capable of powering a wide variety of implantable devices without the need for cumbersome external battery packs and stationary power sources. This device enables patients to have the ability to move about freely without concern for maintaining predetermined positions of internal-external induction coils and external battery packs or other types of power sources.

These and further objects and features of this invention will become more readily apparent upon reference to the following detailed description, with reference to the attached drawings, in which:

DESCRIPTION OF PREFERRED EMBODIMENTS

Specific Applications

Figure 1:
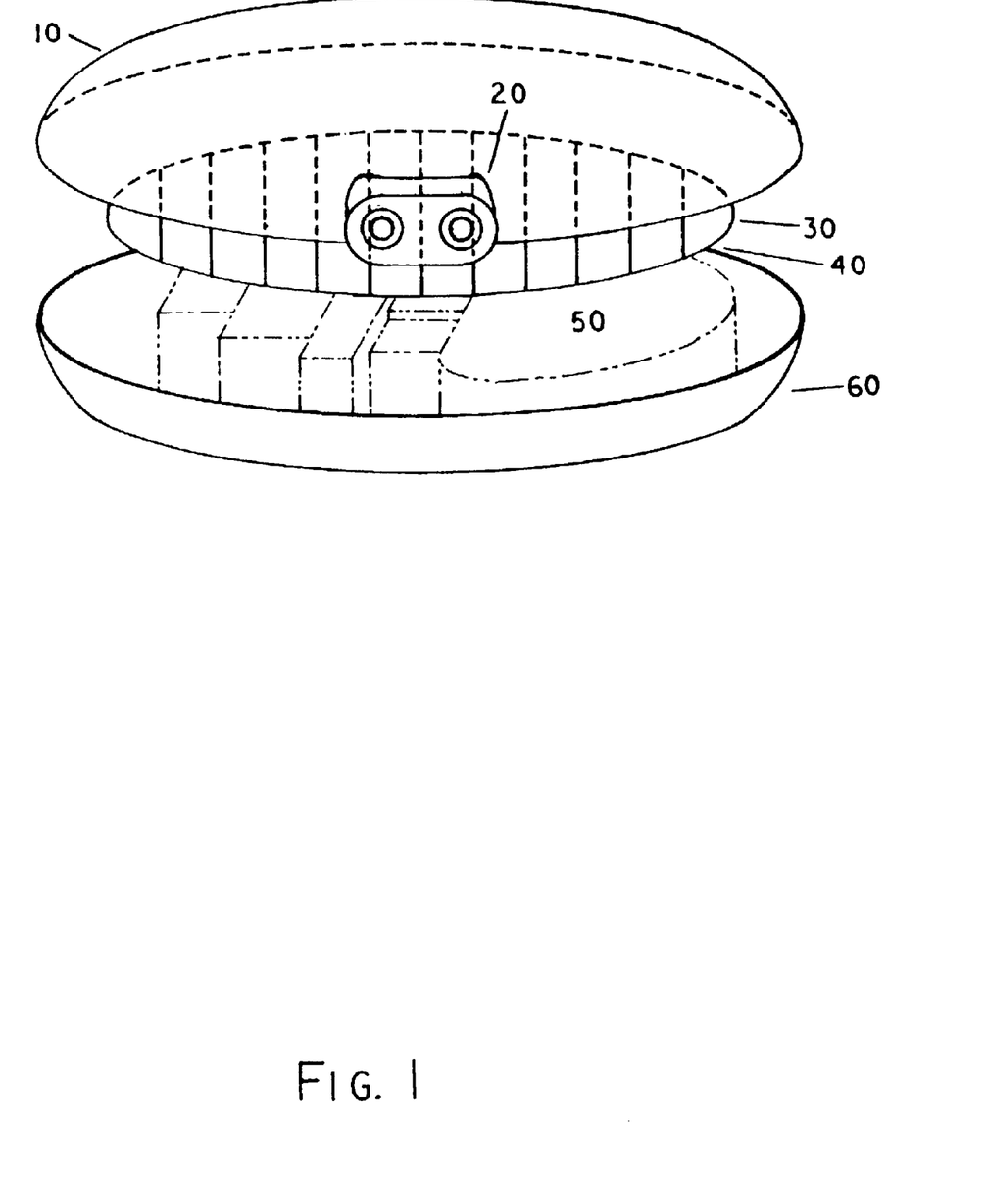
FIG. 1 is an exploded view of a conventional cardiac pacemaker having a top or outward facing half, or the entire case, made of injection molded clear resin.

Referring now to FIG. 1, a typical cardiac pacemaker modified is so that its top 10 is made of a clear resin of the high-impact type, permitting a high percentage of light transmission, while having a high resistance against impact damage. Resins are presently available which can withstand the impact of a rifle bullet fired at a distance of two feet. Leads housing 20 is molded as an integral part of the outward case half, though it can be molded as a separate part. Pacemakers typically have one or two leads, not shown, extending from the case and leading to the heart, depending on the type required: single or dual chamber. Incorporation of the leads housing into one or the other half of the case reduces the number of case parts, and the possibility of case leaking of bodily fluids into the device, which is presently one cause of device failures.

A photovoltaic array 30 can be made from silicon or gallium arsenide or other combinations of materials. This array would have the appropriate cell divisions so that in a "One Sun" condition it can generate a voltage that doubles or triples the full-charge voltage of the battery. Thus, in moderate lighting conditions, it will still generate a voltage equaling that of the battery(s). A thin piece of metal 40 beneath the photovoltaic cells serves to prevent unwanted bombardment of the implant device by electro-magnetic waves (RF) typically encountered when the wearer is going through an x-ray device or any type of metal detectors, encountered at airports or at any location, where electronic security precautions are taken. It will also provide a barrier when the wearer is standing near a leaking microwave oven door. Not shown is an electronic circuit that will permit the cells to provide direct power to the pacemaker's Central Processing Unit should the batteries experience failure. Forward-biasing diodes (not shown) will prevent the backflow of current when the cells are not being exposed to light, in a known manner. This prevents the cells from draining the batteries, which is standard circuitry for all photovoltaic cells, when used to charge batteries. In the event of battery failure, the wearer would hold a flashlight against their skin directly above the implanted device, especially if the occurrence happens at night, so the photovoltaics will continue to operate while the wearer calls for an ambulance or drives to a hospital. The device battery 50 typically occupies 40% to 60% of the inside area of the case. The RAM and ROM chips and the device's central processing unit (CPU) are conventional and, consequently, not shown, since all pacemakers are fairly simple, dedicated computers, commonly referred to as pulse generators. The bottom of the device case 50.

Figure 2:
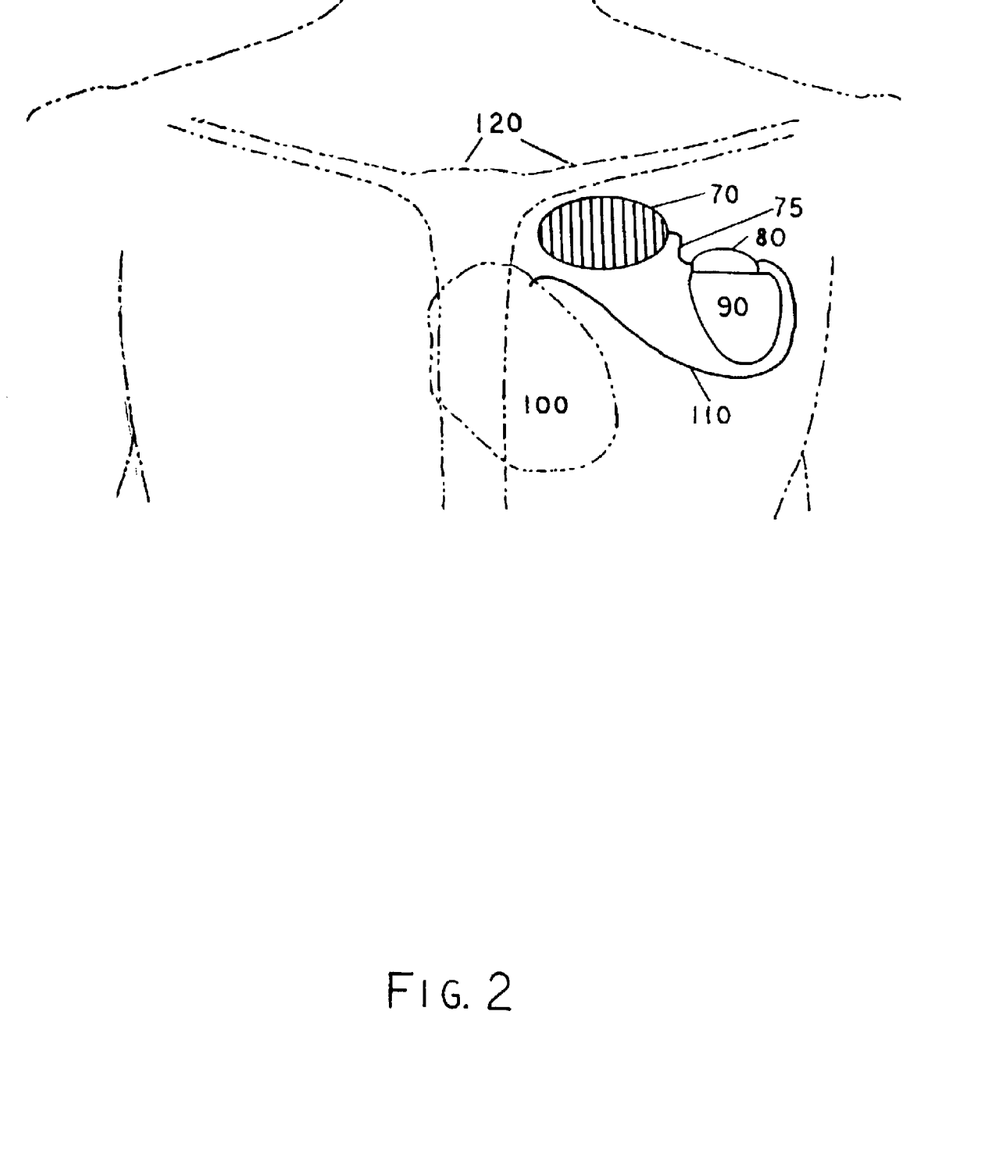
FIG. 2 is a front view of an implanted electronic device having photovoltaic cells are outside the device case.

In FIG. 2 a pacemaker or other implanted device 90, the photovoltaic cells are laminated between sheets of resin 70, and plug into the electronic device's case via a flat ribbon wire 75, with moisture-sealed plug-in connectors in a typical pacemaker lead wire housing 80. This arrangement will be necessary requiring where greater cellular surface area. Encapsulation by cartilaginous body tissue tends to occur as a natural function when any foreign object is introduced, which tends to hold the device in the position it occupied when implanted. A pacemaker lead wire 110 extends into a heart 100 adjacent sternum bone 120.

Figure 3:
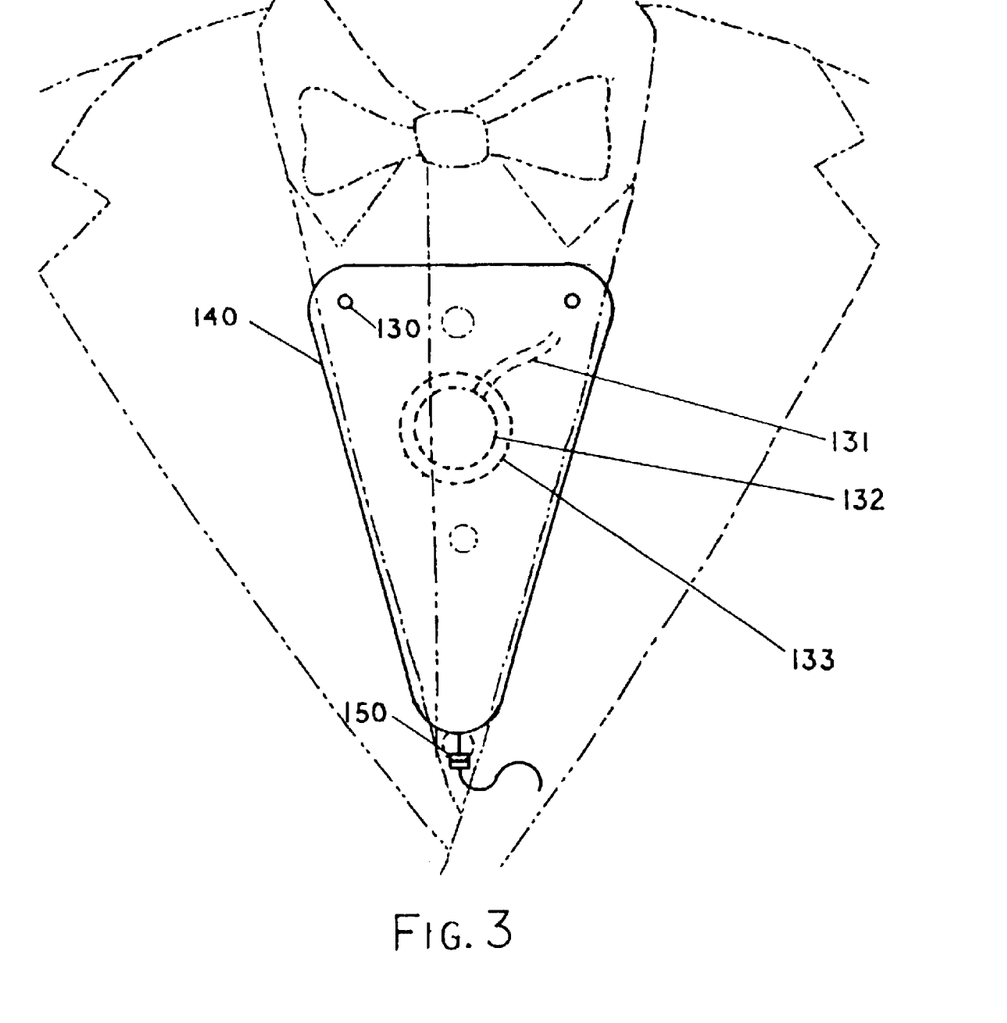
FIG. 3 is a front view of a larger implanted triangular array or stack of photovoltaic cells positioned under the dermis, over the wearer's sternum, for maximum light exposure when the wearer is attired in a suit.

FIG. 3 shows a triangular array of photovoltaic cells 140 designed for maximum exposure to light by a person wearing a suit coat with a bow-tie. Cells 140 are designed mainly for an implanted mechanical heart, but can also be used to recharge batteries in a defibrillator or an insulin pump, typically implanted along the side of a wearer, near the pancreas. A smaller version can be made for juvenile wearers. Array 140 has two holes 130 for receiving stitches to temporarily attach the photovoltaic array to the wearer's under dermis to hold the device in place until it is encapsulated by body tissue.

A two-lead wire 131 extends from the inner coil 132 of fine wires. The size of array 140 permits a large number of turns of wire, should a voltage increase be desired, at the expense of current. An outer resin lamination seal 133 is provided for coil 132. A ribbon wire extends through a hermetically sealed electrical socket 150, which can contain the forward-biasing diode. This wire extends under the bottom of the sternum or between the ribs to an implanted mechanical heart. Or it can extend to a defibrillator or drug infusion pump by passing just under the dermis. These photovoltaics will be made from commercially-available ultra thin cells which are typically 0.007" thick, and be very flexible, partly due to body heat keeping the cells warm. It should be noted that these flexible cells can be laminated between one-half mill thick laminating sheets with a curved bias so they will not tend to stick up at their corners, which are rounded to prevent becoming a source of irritation. Use of a bow tie in place of the conventional pendulum tie is a small concession to enable effective use of this array 140.

Figure 4:
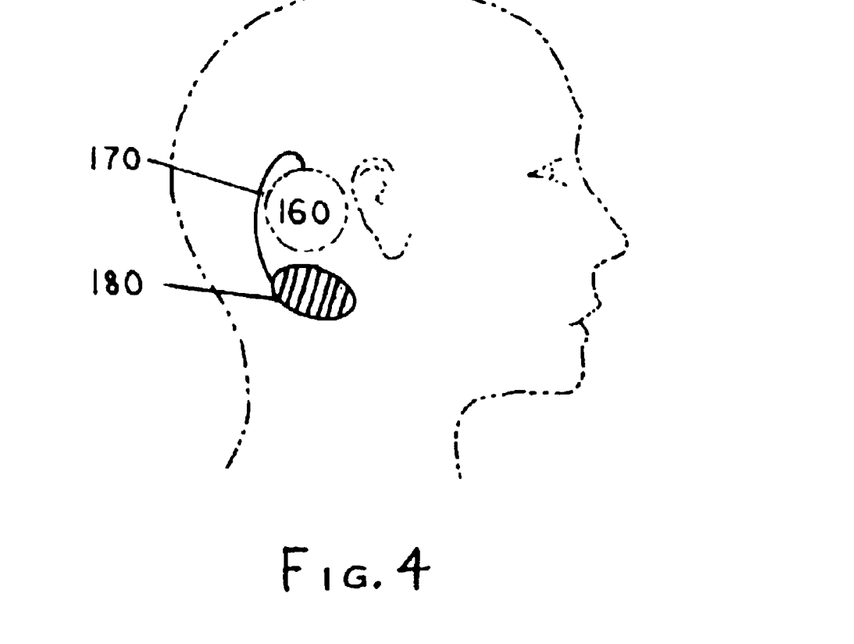
FIG. 4 illustrates positioning of a photovoltaic cell under the dermis along the side of the cranium at the top of the wearer's neck for minimum hair blockage.

In FIG. 4, one of the new surgically implanted hearing devices, currently awaiting Food and Drug Administration approval in the U.S., and from similar sanctioning bodies in other countries, includes an implanted amplifier 160, partly recessed in the cranium. A power wire 170 extends from amplifier 160 a separate small array of photocells 180. More devices show promise of being on the market in the next five years. A promising device by St. Croix Medical Corporation uses transducers implanted through the mastoid bones where vibrations are picked up from bones in the middle ear and fed into an amplifier, partly recessed in the side of the skull for cosmetic reasons. In this device, as in pacemakers, the photovoltaic cells may be implantable inside the amplifier. If that is not considered feasible due to space limitations, the cells can be a stand-alone separate group of cells plugging into the side of the device's amplifier. In this application, the cells may preferably be laminated into the shape of a gradual curve that duplicates the curvature of the cranium. If a dark substrate or superstrate of the cells not used, these very thin cells will not be visible through the skin. With a black haired and or black skinned person, this stand-alone lamination can be positioned lower on he side of the skull or the neck, where hair is short or non-existent.

Figure 5:
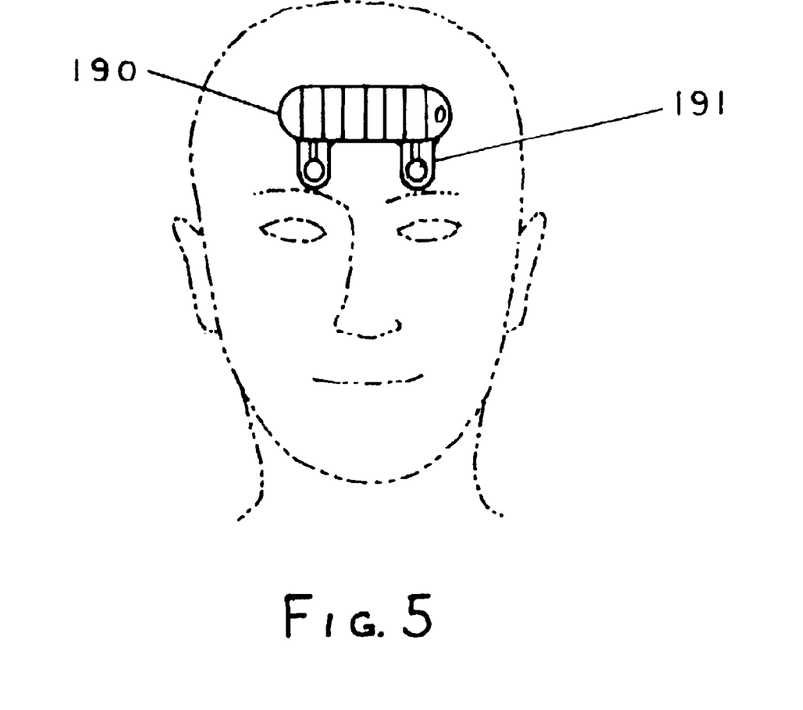
FIG. 5 illustrates positioning of an array of cells placed under skin over the wearer's forehead, a portion of the cranium where hair blockage is not a factor.

In FIG. 5, cells 190 are laminated or molded into the shape of the gradual curvature of the forehead, which permits the wearer to wear a hat, without causing light blockage. Cells power a pair of devices 191.

Figure 6:
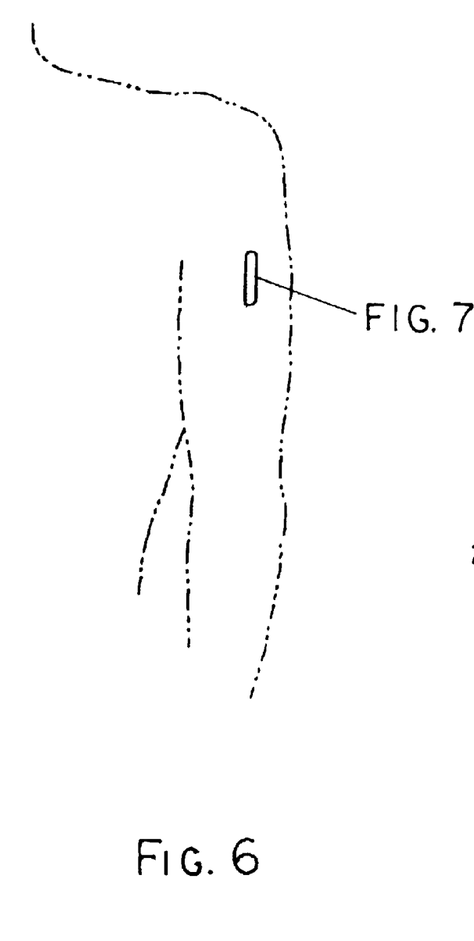
FIG. 6 illustrates positioning of a tubular glass or resin capsule containing transceivers in a person's left arm with used to transmit nerve impulses across the gap when the nerve is severed.
Figure 7:
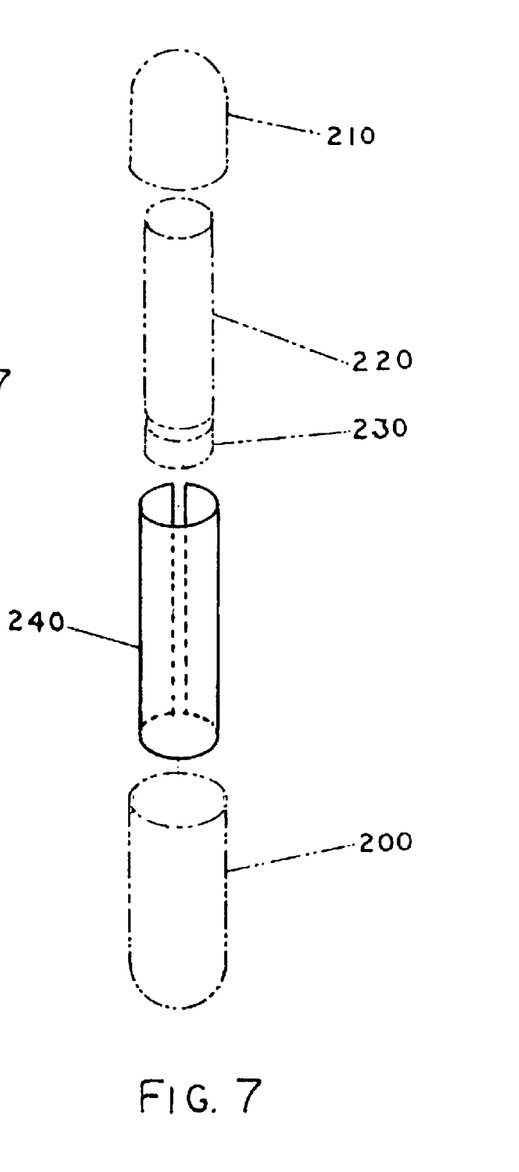
FIG. 7 is an exploded view of a transceiver, including tubular solar cells which will receive light through the skin, when placed on the outward side of an appendage.

In FIGS. 6 and 7, a tubular glass or resin transceiver case 200 is implanted under the skin, preferably on the outside of a left arm, positioned forward of lateral to avoid side impact. Case 200 includes an upper closure 210, which confine a transceiver 220 and a battery 230 (or antenna) that is surrounded by cylindrical solar cells 240, which assure that part of the surface of all cells in the array are exposed to approximately the same amount of light. This is important if the cells are wired in a series circuitry that they run circumferentially around a tubular configuration, so all the cells get exposure to light. It is useful to note that the contact grid wires can be far enough apart so that radio waves can pass between the grids, especially if the positive and negative grid wires are aligned atop of each other. Case 200 can be placed in most locations of the human or animal body. The shown example is circular for structural strength, but can be an oval of nearly symmetrical shape of a near-flat oval.

Figure 8:
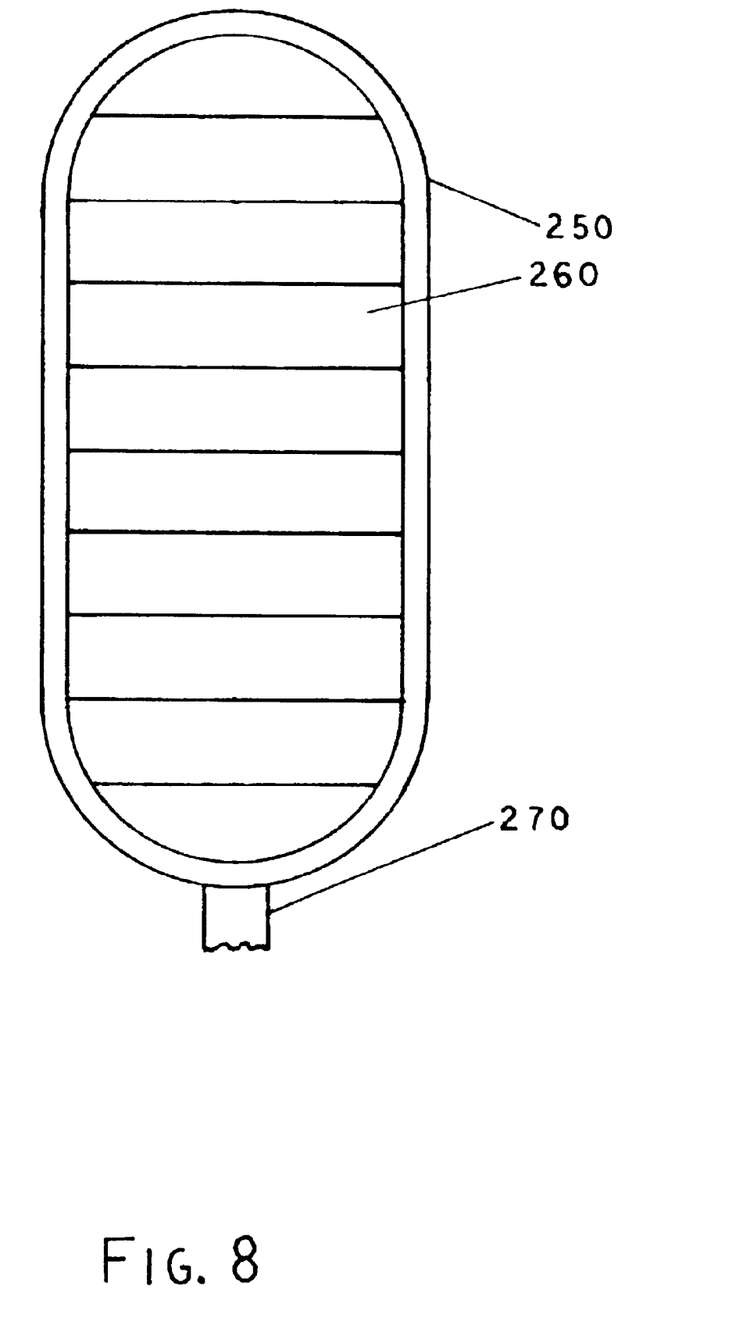
FIG. 8 is a front view of a double scale oval voltaic for pacemakers & defibrillators with eight cell divisions and a typical two strand ribbon wire leading from the cells.
Figure 9:
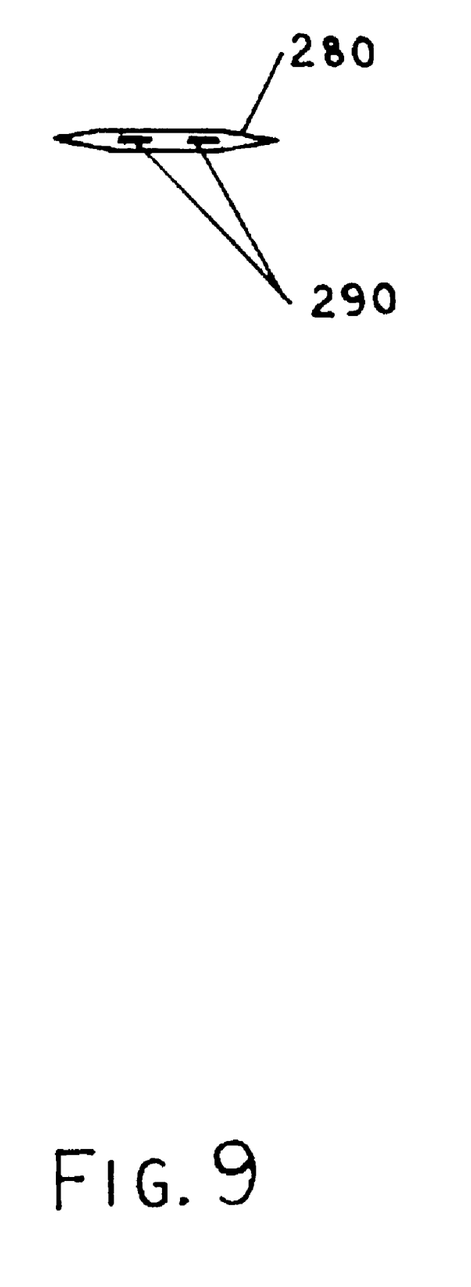
FIG. 9 is a cross-sectional view of a flattened, two-strand ribbon wire encased in a resinous material.

In FIGS. 8 and 9, a photovoltaic array 250 is laminated between layers of light-transparent resinous material of a larger size, and comprises of eight cells 260 which may power a device with larger power requirements. A special flat ribbon wire 270 connect array 250 to the device (not shown) that is powered. Ribbon wire 270 includes two plated ribbon wires 290 encased in a sheath 280. The gradually tapered sides of ribbon wire 270 is desirable to get a liquid seal between the wire and the laminated solar cell laminating sheets of resinous film, necessary to prevent the ingress of bodily fluids.

Figure 10:
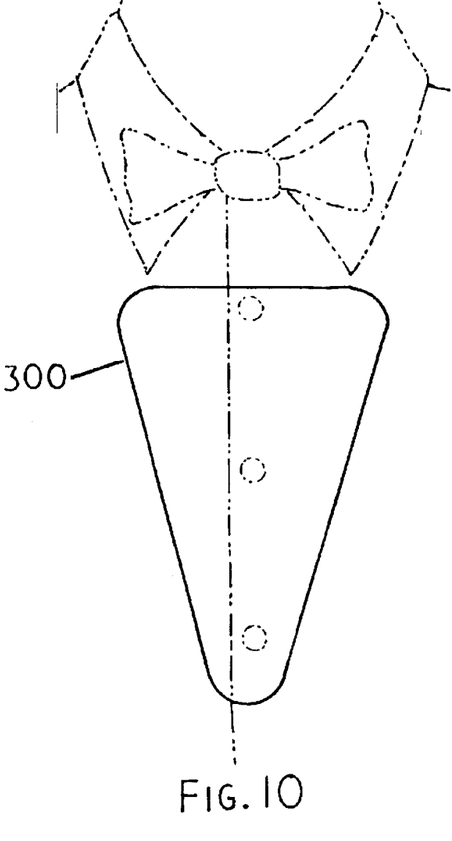
FIG. 10 is a front view of a multi-layered, triangular transparent solar array, providing approximately two square feet of solar surface area.
Figures 11, 12:
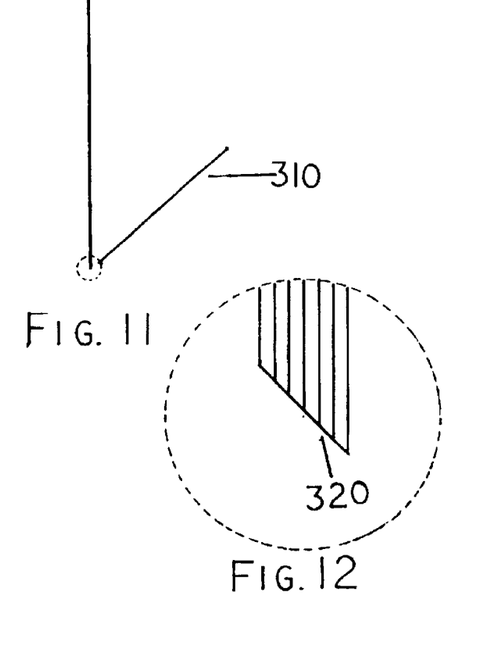
FIG. 11 illustrates a desired 45° angle of the multi-layers of stacked transparent solar cells.
FIG. 12 schematically illustrates six layers of solar cells with the desired 45° angle.

FIG. 10 shows a triangular array 300 (shown in FIG. 3) positioned over the sternum. FIG. 11 illustrates the layers of the solar array placed at the ideal 45° angle 310. FIG. 12 shows a six layered array 320, which can comprise any number of layers, depending on the stiffness resulting from the multiple layers, and the degradation of the amount of light received by the bottom layer as the number of layers increases.

Figure 13:
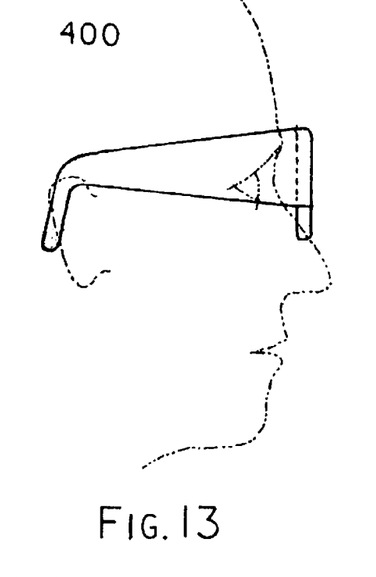
FIG. 13 is a side view of a person wearing eye glasses that illustrates an area available for implanted solar cells in clear plastic.
Figure 14:
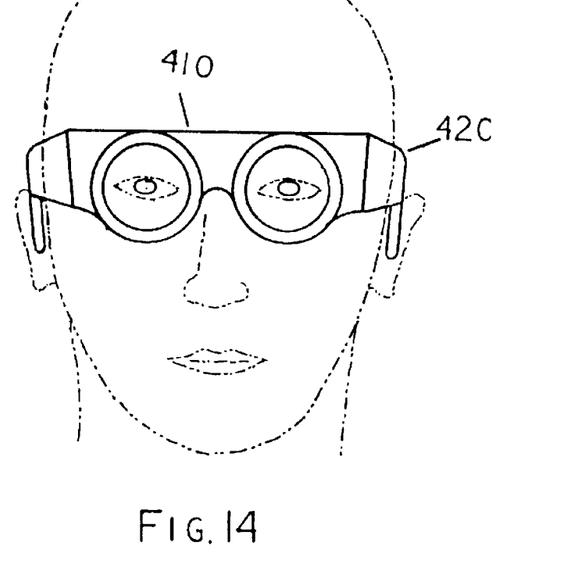
FIG. 14 is a front view of the FIG. 13 depiction.

FIGS. 13 and 14 show a user 400 wearing eye glass frames 410 designed to provide the maximum amount of surface area for embedding solar cells on both sides of the side frames 420. The frames preferably include a battery holder and/or a plug-in socket for a separate battery connector for a battery carried in a shirt pocket of on the wearer's belt.

Figure 15:
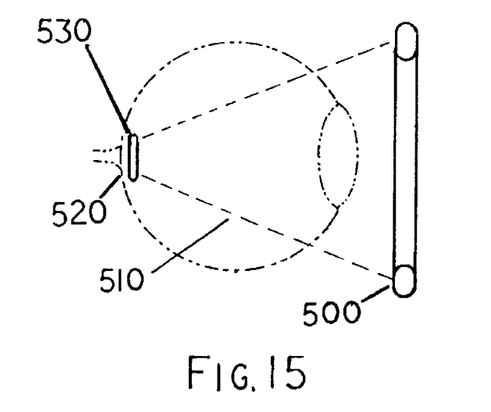
FIG. 15 is a side view of a lens frame-embedded coil that transmits electrical energy to the secondary coil, embedded in a plastic implant support structure, feeding power to the photo light receptors.

In FIG. 15, eyeglass frames 500 have an embedded primary induction coil that transmits electromotive force (EMF) into a secondary coil 520 located on the periphery of a retinal implant 530, providing the amplification of light 510 picked up by the numerous photo-receptors.

Figure 16:
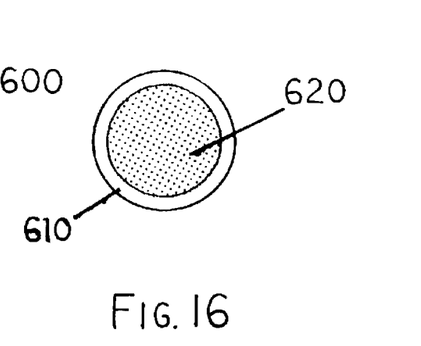
FIG. 16 is an enlarged detail view of a retinal eye implant having an induction coil at the periphery, with numerous central photoreceptor cells.

A retinal implant 600 (FIG. 16), similar in size to an ordinary contact lens, is turned so its concave side faces outward, its convex side in electrical contact against the retina/optical nerve. The secondary coil is represented by the ring surrounding the photo-receptors 610, with its central area 620 having numerous light gathering photo-receptors.

General Discussion of the Invention

For many applications, such as mechanical heart pumps, and limb actuation devices, or any large power consuming electronic device, a larger triangular array, shown in FIG. 3, consisting of multi-layers of transparent cells, positioned atop each other, several layers deep, located over the sternum, will be advisable, due to the power demand of such pumps, presently requiring external battery packs. Also, implanting larger thin, flexible arrays under the dermis on the wearer's back will be feasible, since this is the largest relatively flat surface area of the human body, and is least articulated. The total solar surface area of multi-layers of these triangular cells will exceed two square feet when implanted over the sternum, and up to six square feet of surface area for these multi-layered cells, when implanted under the dermis of a wearer's back. Picture a six-layer solar array approx. 0.030" total thickness, remaining flexible partly due to body heat. This much surface area might be needed for maintaining the charge level in mechanical hearts or implanted batteries for mechanical arms, etc. Also, these implanted cells can (via induction coils) generate, power while implanted inside the body, then transmit the current outside the body, into a device motor positioned in a mechanical limb, strapped to the wearer's body.

It should also be noted that a flat induction coil can be located on the back (inward) side of any implanted solar array, so it can transmit power into a bodily device for which the cells are positioned directly over such device, without the solar array being physically attached to the implanted device. The second induction coil can be positioned on the surface or directly underneath the device cover, if the cover is non-metallic, so electromagnetic waves can "jump" from the solar positioned flat coil if it is aligned over a second, device-coil. Axial alignment of two induction coils plus being close together is necessary for the most efficient transfer of electrical energy, with the least transfer loss. Having the solar array's induction coil larger than the implanted device induction coil will permit more axial off-center alignment and spatial separation of the coils. Also, having more turns of the secondary coil will permit a jump in the voltage as it passes between the two coils.

Regarding the solar array shown in FIG. 5, which is implanted under the dermis of a wearer's forehead, that array is designed to (among other needs) provide power for new retinal eye implants presently in the experimental stage. Note a small, flat, induction coil is shown in the two downward extensions of that array, designed to be less than one inch from a similar flat coil that surrounds the retinal eye implant, ideally positioned around the periphery of the retinal implant photo-cells, to power them. Note that one coil is positioned to be directly above each eye, to reside approximately behind each of the wearer's eyebrows, thus being positioned as close to the retinal-implant coil. Also, these downward positioned coils can wrap around and under the top of the eye socket, bringing the coils within ½" inch of the eye implant coil. And since the power generated from all solar cells is d.c., a small, possibly crystal oscillator, oscillating at perhaps 60 cycles per second or another speed, will convert the power from the cells into a.c., so the power will "jump" across from one coil to the other. Of course, the retinal eye implant coil will also have an inverter, converting the power back into d.c., if that is deemed desirable to electronically excite the light photo-receptors attached to the back of the retina. Such cells might be powered from pulsating d.c., rather than a.c., if their design permits, reducing the number of inverter parts, even though they will be micro-miniature in size. Formerly blind implantees may enjoy superior night vision to normally sighted individuals, by stimulating these photo-receptors to respond to very weak incoming light.

This triangular solar cell implant positioned over the sternum, or elsewhere in the body, will not only be multi-layered, but each successively lower layer of cells will be slightly larger in dimensions, with edges terminating at a 45° angle, so light may enter their respective edges and refract across the surface of each layer of cells, forming a light trap: since light will be entering between each layer, from all the sides simultaneously, and being of uniform intensity, the light will not depart the layer's opposite side: thus, a "light trap."

Continuing on the subject of retinal eye implants and a dual method of providing power to reach their photo-receptors, a second method of transferring light to the multi-layered induction coil calls for the primary induction coil to be implanted in both of the wearer's plastic eye glasses rims. This second method has the advantage of being in perfect axial alignment with the retinal implanted coil, with the disadvantage of being farther from the implanted coil. However, the external coil, which is fed current both from solar cells imbedded in the eyeglasses side frames being of maximized width, to give them more surface area. These glasses frames can also have a small battery holder on the side frames or an electrical plug, permitting a battery carried in the wearer's shirt pocket or attached to the wearer's belt that supplies power to the eye glasses frame coil, thus providing a dual source of power to the retinal implant: solar cells for daytime powering; external battery for night-time powering.

The power supply is adapted to power an implanted battery-powered electronic device. If the cells generate excessive current above the electronic device requirements, conventional circuitry should be included to convert surplus current to higher voltage outside the group of cells. The powered electronic device should have a reactance switching circuit, so that the current delivered from the cells can bypass the battery to enable the cells to power the device directly, if the battery develops a short or an open circuit.

Tests

My tests have demonstrated that a strong Electro Motive Force (EMF) is present at a distance of six inches using two one-inch by one-fourth inch thick ring magnets. One was glued inside a small plastic cup and set afloat in water. A second identical magnet was positioned on the surface, oriented in its repelling position. The cup-borne magnet was repelled rapidly. This demonstrated that the EMF field actually exceeded six inches. When one considers the extremely small amount of electrical energy needed to amplify the weak current at the photo-receptor site, it becomes apparent that a numerous turn induction coil embedded in plastic eye glass lens will duplicate this magnetic field, and can increase the micro-volts at the implant site, if the secondary coil has far more turns of a 0.005" coated copper wire than the primary coil. It should also be considered that ferrous oxide material can be embedded in the resin before the plastic lens frames are injection molded, increasing the EMF field at the primary coil site.

In my design, the internal battery, (inside the mechanical heart), provides temporary power for the device when the wearer removes the external belt while showering, swimming or to replace one belt pack with a spare one, which has been hooked up to an external charger and recharged. Thus, it is clear that a back-up power source consisting of an internal battery is a wise design approach. The external battery pack-belt, if used alone, also presents a problem when the wearer is asleep. Tossing and turning may cause the external and internal coils to become sufficiently misaligned to cut off the flow of current to the mechanical heart. The only apparent solution is for the wearer to slip on a tight fitting sleeved vest with straps on both sleeves, tied to raised bedside railings, to prevent the wearer from rolling-over movements while asleep.

In general, this new charging technology is directed to subcutaneously implantable solar cells having a wide array of various configurations. Each of the many types of variations are configured to supply a predetermined amount of power that corresponds to the operating power and battery recharge requirements of the desired implantable medical device. Many variations and modifications have been tested to ascertain the desired configurations for different externally worn and implanted solar cell devices.

Regarding my new charging technology, initial tests were performed in the following manner: a volt-ammeter was attached to small amorphous silicon cells that were placed under a larger sheet of Plexiglas. Atop this thin Plexiglas were placed successive layers of skin from the breasts of birds. With each additional layer of skin, the drop in current generated by the cells was recorded. The short coming of this first test was the fact that the skin from birds is without pigmentation due to feather coverings, explaining why multiple layers were used, whereas human dermis has varying degrees of pigmentation. Next, I placed a small cutout section of a man's tee shirt, and recorded the current drop (very small). Then I added a 12 ounce single layer white dress shirt over the above and found that I could still generate about 86% of the current with these three barriers in position, compared to what was generated before coverings were placed over the cells. Further tests have demonstrated that the One Sun sky condition: sun is at its zenith without sky obscuration (clouds or dust), the output of the cells, in terms of their voltage should be typically two or three times the fully charged voltage of the implanted battery, due to light loss from penetration of skin and thin white clothing. After the clothing and light barriers are taken into account, the voltage under bright light will still exceed that of a fresh battery. This ideal charging voltage for longevity should not exceed the fully charged rated voltage for the battery under the brightest lighting conditions. The charging voltage will not exceed the full-charge rating, by virtue of a resistor or other power limiting components, which is a practical approach, considering that d.c. voltage comes from the voltaics and can be reduced by a very small wattage resistor, approximating the diameter of ordinary pencil lead.

The documented results of only the most recent implanted solar cell tests are included in the following text.

A test was conducted using this investigator as the subject in the following manner: I placed a single solar cell (single-crystal type) measuring 2 cm×4 cm inside a clear plastic case of slightly larger dimensions, with positive and negative wires extending outside the case, and outside my mouth, Then, they where attached to a sensitive volt-ammeter, with the cell facing the sun under a One-Sun sky condition at 11:00 a.m. on Apr. 12, 1999 at Merritt Island, Fla., located at 26° degrees north latitude.

Apr. 12, 1999 Merritt Island, Fla. 26° North Latitude. A One Sun Sky

Readings Were

| | |
|---|---|
| 0.6 volt @ 182 mA (182,000 uA) | Outside my cheek |
| 0.4 volt @ 6 mA (6,000 uA) | Inside my 3/8" inch thick cheek |

The test was performed with the cell outside my mouth, then repeated one minute later with this encased cell positioned inside my mouth—between gum and cheek. This time the readings were: 0.4 volt @ 6 mA, as shown above. This test was most relevant, since the thickness of my cheek is about 3/8" inch, measured by a caliper—much thicker than the typical thickness of body dermis where cells will be implanted. Also, this single cell was approximately one-half the size of the 1"×2" implanted cells to power small current demand implantable devices. Fatty tissue will be separated from the outer dermis, so the cells will typically be surgically implanted to a depth of only 1/8" inch. (Fatty tissue provides less light barrier than lean tissue.) This particular test was conducted with implantable cranial devices in mind (hearing aids, for example, but not limited to.

Subcutaneous cranial locations will permit the use of short, flat ribbon-type wire leads. However, the test is valid for cell(s) placed anywhere beneath the skin, not covered by clothing. The cells can also be positioned anywhere around the side of the skull and permit the patient to wear a hat without undue blockage of light. Or, the cells can be placed so as to cover part or most of the top of the skull, or the forehead, if more power output is needed in the cranial area.

Light penetrates scalp hair with good success, unless it is thick and black. In such cases, the cells can be implanted subcutaneously under the lower side of the cranium, (below and behind the ear or upper part of the wearer's neck), where hair can be kept to a minimum length, without being cosmetically objectionable or in the forehead. The scalp will also be the logical location for cells used to power brain stimulation or brain pain suppression devices, some devices are already on the market by Medtronic Corporation, and others. Thus, the amount of current generated with this behind-the-cheek test of 6 milliamps (6,000 micro-amps) is far in excess the amount needed to keep the typical pacemaker battery with a current consumption rate of only 20 micro-amps, fully charged. The cheek positioned small cell produced approximately 300 times more power than is needed. I estimate these cells will only require an average of two minutes of sun or bright indoor light exposure per month—either will be suitable.

Going back to pacemaker defibrillator implantation of cells in the upper chest area, tests have shown that sufficient light will penetrate the wearer's outer shirt and undergarment and still produce useful amounts of current, with the exception of when the person is wearing a heavy suit coat or overcoat. One test with cells placed beneath undergarments, and under a summer-weight tan suit coat produced 0.85 Volt, from three series-wired 1/3 inch square cells, capable of 1.9 no-load volts. If a pacemaker battery depletes at an average rate of only 0.2 tenths of a volt in six years, that means its battery drops only 1/10,950th of one volt per day. Therefore, the photovoltaic cells need only be exposed to moderate intensity light, indoor or outdoor type, occasionally.

Another series of tests were conducted where moderate indoor lighting for the original series of tests consisted of a 100 W tungsten filament reading lamp with the cells positioned precisely 24" inches from the bulb, without light blockage from the shade. Thus, a situation will never exist where the cells need to be constantly exposed to light. A wearer will be exposed to hundreds of times that much light duration every month. Even the most restricted shut-in wearer will get far more exposure than is needed to keep the battery(s) charged. This Indoor Test using a single solar cell (2 cm×4 cm) extruded-crystal type, positioned 24" inches from a new 100 watt lamp bulb produced the following readings:

Indoor Test: Cells 24" Inches from 100 W Tungsten Filament Light Bulb

| |
|---|
| Outside Cheek: .24 volt. > Inside Cheek: .05 volt. (single solar cell) |
| Outside Cheek: 1,770 uA > Inside Cheek: 46 uA (twice typical amount needed) |

This equals 46 uA micro amps, about twice the current demand of the typical pacemaker. With cells, in most cases, one-third the size of a business card, describing a 1" inch×2" inch oval, laminated between possibly polyester or Mylar® layer(s) for electrical insulation or another suitable electrical barriers, the power output will be double the above readings. Even in cases where the pacemaker is implanted deeper into the chest (for cosmetic reasons, so a bulge will not be visible), the cells can still be implanted just under the skin, to a depth of only 1/8" inch, only one-fourth the depth of the cells in my inside cheek test.

A duplication of the above Merritt Island, Fla. test, conducted at Columbus, Ohio (40° north latitude) two days later also under a One Sun sky condition produced the following results:

Florida Test Repeated May 2, 1999 at Columbus, Ohio (40° N Lat.) One Sun Sky.

| 0.50 V @ 156 mA (156,000 uA) | Outside my cheek |
| 0.25 V @ 1.8 mA (1,800 uA) | Inside my cheek |

Regarding the placement of photovoltaic cells under dark-skinned people, the cells can be larger, which will not present a problem. The size recommend for Caucasian pacemaker-defibrillator wearers will be approximately 1"×2". Doubling that for dark skinned people, means cells 2"×4", still comfortably small in size, considering their flexibility and the ample space available around the upper sternum area. This larger size will not be uncomfortable. Moreover, multiple 1"×2" photovoltaic cells may be used and electrically connected in series or parallel as may be required by the particular application. And, those people having darker skin pigment levels can hold a small flashlight over the implanted cells for about two minutes monthly, to accomplish similar results.

Columbus, Ohio Test Repeated 12:00 Noon May 11, 1999 (40° N Lat.) One Sun Sky

| 0.51 V @ 176 mA (176,000 uA) | Outside my cheek |
| 0.26 V @ 1.7 mA (1,800 uA) | Inside my cheek |

Using the same single cell as in the above test, this test was repeated standing in the driveway near a tan painted house, performed at twelve noon in the presence of a witness: Mr. David E. Dolle, a retired engineer, used by Dynatron for drawings.

Columbus Test Repeated at Lancaster, at Ohio 12:00 Noon May 12, 1999 (39.8° N) Sky Condition: Clear of Clouds, with Visible Haze.

| 0.53 V @ 175 mA (175,000 uA) | Outside my cheek |
| 0.30 V @ 1.5 mA (1,500 uA) | Inside my cheek |

Numerous other tests were conducted over the many years this project was under development, not included here. Regarding the manufacture of the final design of these photovoltaics, Iowa Thin Film Technology and other companies could be a made capable of manufacturing these cells, minus the special lamination(s).

In other variations of the present invention, the photovoltaic cells may be integrally formed into the plastic cases of the implantable medical device that is implanted subcutaneously. In this configuration, the present invention eliminates the need for additional subcutaneous wiring. Moreover, with minimized wiring configurations, less power loss is experienced as power is transmitted across the shorter wire leads. In one possible modification, the photovoltaic cells may be contained within a clear or transparent plastic case that surrounds the medical device to be implanted.

If the cells are not placed on or within the clear plastic case, they can be in their own laminated encasement located near or distal to the device and plugged into the device they supply via a short or long transparent ribbon wire, leaving no visible evidence on the surface of the body. Anyone familiar with solar cells will have noticed that the back substrate layer of those cells is typically dark brown or green. They are manufactured this way based on the assumption they will be exposed to direct outdoor sunlight while in a fixed position relative to the sun. The dark coloring serves to absorb rather than reflect light. Light reflection will not be a problem because of the tissue above implanted cells. The removal of this unnecessary coloring has cosmetic value, since the above mentioned coloring would make the cells visible under the skin of fair-skinned people. These cells can be mostly transparent, except for their pick-up grids or "fingers" affixed to the outward facing side, which can be very thin. When cells, minus the coloring, are placed under the skin, the dermis and blood flowing through the capillaries directly over the cells will shift the color of incoming light to that Kelvin range where silicon cells are most responsive: 1500 K to 1800 K—orange to cherry-red. Cells recharging a mechanical heart battery, and an insulin pump battery, must be larger than those for pacemakers or defibrillators, with much more surface area. For those devices, a larger thin array, (0.012" inch thick and flexible), may be placed under the skin, over the sternum—the obvious place for implanting a relatively large array that may be up to six inches across its narrower top side and extending downward up to seven inches for (adult size), more pointed end facing downward. For this configuration, a child and adult sizes will be necessary. This is the logical placement for recharging a heart pump battery for two reasons: when the pump is implanted, the sternum is sawed in half vertically down its center, leaving the ribs on both sides attached, then pulled apart for access into the thoracic cavity. After the pump's emplacement, the sternum is closed and stapled or wired together. Before this closure, a two-lead thin ribbon wire will be inserted around the bottom of the sternum halves and plugged into a hermetically sealed miniature flat socket, plugging an inside heart battery, and into the solar array. The second reason is when the wearer is attired in a suit coat, the edge of the two lapels form two sides of a triangular area, wherein there is the least clothing blockage of light to the cells. In the case of a male wearer, if the person will wear a bow tie instead of the conventional pendulum tie, it will not block light access to the cells, leaving only a white undershirt and preferably white outer dress shirt providing minimal light blockage. This change in neckwear represents a minor compromise in the way a person dresses. It should be kept in mind that a mechanical heart and an insulin pump will be the most current-demanding devices implanted in the body, requiring this small consideration, partly because the heart pump must run constantly, unlike pacemakers and defibrillators, except for their monitoring circuitry.

Cells for bodily implantation can involve a combination of series and parallel wired circuits, perhaps wired in what are called "strings," capable of producing an outside-the-body voltage at least 100% greater than that produced when implanted, since the voltage generated under the skin must equal or exceed the fully-charged voltage of the battery. If a single wiring strategy is preferred, parallel wiring will best insure that adequate current is generated, with a voltage-doubler circuit employed outside the cells to boost voltage at the expense of current output. Pacemakers typically use a single cell 2.8 V Lithium-Ion battery when fresh, and with voltage doublers, routinely increase the voltage to five volts going through the wire into the wearer's heart. Also, the covering of the implanted cells can be tinted so as to shift the incoming light to that color, which produces the best spectral response in a particular type of cell. Although blood passing through the capillaries directly over the implanted cells will benefit silicon cells, without any case tinting of their non-conducting lamination covers, are slightly more responsive to the unabsorbed light passing through the skin. Other constructions of solar cells, such as those made from gallium-arsenide are more responsive to light in a wider portion of the light spectrum, though slightly more responsive to light in the blue-green portion of the spectrum. Thus, shifting the color of incoming light will be a straightforward matter by using tinted plastics, all of which provide good electrical insulation. Tefzel™ (registered trade mark of The DuPont Company) is one encapsulating material presently used on outdoor cells, and can possibly be a half-mil thick lamination on both sides of those cells, possibly laminated to Mylar® (a small molecule resin with high gas-barrier properties. Mylar balloons are now a common sight because Mylar has high barrier properties to gas and liquids.) so bodily fluids can not short circuit the cells. A forward-biasing diode(s) will prevent any back flow of current when the cells are in low light. This Tefzel™ or other plastics can also be molded in a convex shape so it acts as a magnification lens, multi or single-faceted type under the skin. However, tinting cells involves a trade-off, since it reduces the amount of light energy that can pass through.

Preferred solar cell types are those which are most responsive in low-light conditions, including those with sintered or crenellated surfaces, which give the cells more surface area for a given linear dimension. Cells made of gallium arsenide, with their band gap of 1.4 eV (electron volts) will be appealing, although their cost and toxicity of Arsenide is a contra-indication to their use. However, the small amount of cell area required is an argument in favor of their use. Gallium-arsenides have much higher range of solar absorption than silicon, with conversion efficiencies around 26%. Gallium-arsenide 1As used in multiple cell-spectral separation will be desirable, if the outer lamination(s) are total. In any case, the search for new photovoltaic cell materials is ongoing, with silicon an excellent choice for the present because of its inert, non-toxic nature.

Regarding light skinned wearers who may get excessive sun exposure to the cells, an off-on soft convex shaped button can be provided on the solar array or on the device case (facing outward), permitting the wearer to switch off the electrical output from the cells by pressing this button through the skin. The wearer will be able to feel the location of the implanted cells, and the location of this button, perhaps placed at the junction point where the ribbon lead wire attaches to the cells, or on the plug that attaches the cell(s) into the device case. Thus, the wearer can switch off the cells, if that proves desirable, though a simple resistor can be in the circuit to reduce the maximum voltage output if desired, keeping in mind that the actual challenge is to prevent excessive charging of the battery.

Rechargeable Lithium-Ion batteries have a shelf life of up to twenty years. When used in an electronic application without the benefit of a practical recharging means, their life span averages about ⅓ of that. However, their life can be safely doubled, up to twelve or fifteen years in the body by recharging, cutting the number of life-threatening surgical replacements approximately in half.

Also, using a new trickle-charging method, less expensive Ni-Cad batteries may be used. According to the reference work: "The Complete Battery Book," by Richard Perez, published by TAB Books, Inc, page #45, the sealed pocket plate type Ni-Cad battery has a calendar life of up to twenty years, if current demand is low and the battery is used in a float-charge installation (not deep-cycled), which will be the case with this invention. This equals or exceeds the lifespan of the best Lithium-Ion battery.

This is very important both from the standpoint of cost savings to the individual and insurer, and in the reduction of repeat traumas from surgeries. This surgery for replacement of pacemakers, especially in older people, is fatal about 10% to 15% of the time. This investigator presently knows of two pacemaker wearers in their mid-eighties whose batteries are below the replacement voltage levels. However, their health is so fragile surgery is contraindicated, leaving them to expire as a result of gradual battery failures. Thus, it is abundantly clear that this invention, using specially designed photovoltaics constructed in several configurations for the particular body device they charge, will save thousands of lives per year.

While only preferred embodiments of this invention have been shown and described. Obvious modifications thereof are contemplated within the scope of the appended claims.

I claim:

1. An implantable power supply adapted to be implanted subcutaneously within living tissue, comprising a thin photovoltaic cell encased in a case formed of a lamination of a plurality of thin plastic layers, each layer being translucent in the area covering said cell, such that the power supply is sufficiently flexible to conform to body contours.

2. The implantable power supply of claim 1, further including a plurality of said photovoltaic cells superposed on each other, said cells being translucent.

3. The implantable power supply of claim 2, said case being tinted to a color in the spectrum which produces an optimum spectral response in said cells.

4. The implantable power supply of claim 2, wherein each photovoltaic cell has edges terminating in a 45° angle.

5. The implantable power supply of claim 2, wherein the case thickness is approximately 0.012".

6. The implantable power supply of claim 5, wherein the case has a generally triangular shape and is adapted for implantation over a human sternum.

7. The implantable power supply of claim 1, further including an induction coil adapted to power an electrically-operated device that enhances bodily functions, said device being located externally on a human body.

8. The implantable power supply of claim 1, including holes formed in the case adapted to accept stitches sewn through the holes to maintain placement of the power supply in a fixed location.

9. The implantable power supply of claim 1, wherein said case has a convex, thickened topside providing higher impact resistance and serving as a focusing lens for incoming light.

10. The implantable power supply of claim 2, wherein said cells are wired in a parallel circuit so as to minimize current flow blockage should they be subjected to physical damage.

11. The implantable power supply of claim 2, wherein said power supply is adapted to power an implanted battery-powered electronic device, and said cells generate excessive current above the electronic device requirements, and including means for converting surplus current to higher voltage outside the group of cells.

12. The implantable power supply of claim 11, wherein said electronic device has a reactance switching circuit, and wherein the current delivered from the cells can bypass the battery to enable the cells to power the device directly if the battery develops a short or a open circuit.

13. The implantable power supply of claim 1, including an off-on switch, thus enabling operation of the power supply by pressing the cutaneous layer directly over said switch location.

14. An implantable power supply adapted to be implanted subcutaneously within living tissue, comprising a thin photovoltaic cell encased in a case formed of a lamination of a plurality of thin plastic layers, each layer being approximately 0.5 mils thick and being translucent in the area covering said cell, and said photovoltaic cell being approximately 0.007" thick, such that said power supply is sufficiently flexible to conform to body contours.

* * * * *